United States Patent [19]

Fisher et al.

[11] Patent Number: 4,900,830
[45] Date of Patent: Feb. 13, 1990

[54] PROCESS FOR LABELLING SULFUR-CONTAINING COMPOUNDS

[75] Inventors: Abraham Fisher, Holon; Ishai Karton, Nes Ziona, both of Israel

[73] Assignee: Israel Institute for Biological Research, Nes Ziona, Israel

[21] Appl. No.: 114,479

[22] Filed: Oct. 28, 1987

[51] Int. Cl.$^4$ .................. C07D 495/10; C07D 497/10
[52] U.S. Cl. ........................................ 546/18; 346/16; 346/17; 549/30; 549/40; 540/466; 540/543; 548/409; 548/950; 548/958
[58] Field of Search ............... 546/16, 17, 18; 349/30, 349/40; 540/466, 543; 548/958, 950, 409

[56] References Cited

FOREIGN PATENT DOCUMENTS 0189370 7/1986 European Pat. Off. .............. 546/18
0205247 12/1986 European Pat. Off. .............. 546/18

OTHER PUBLICATIONS

March, "Advanced Organic Chemistry", 3rd Edition (1985), (McGraw-Hill), pp. 1108 and 1089-1080.

*Primary Examiner*—Robert T. Bond
*Attorney, Agent, or Firm*—Sheldon & Mak

[57] ABSTRACT

The invention thus provides a process for obtaining the preferential replacement by isotopes, of at least one of the hydrogen atoms selected from the group consisting of those attached to the α- or α'-carbon atoms in a compound containing the structural moiety (I)

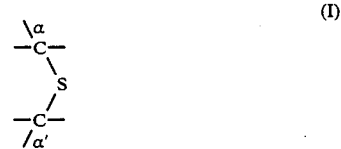

which comprises the steps of oxidizing the compound to the corresponding sulfoxide or sulfone which contains the corresponding structural moiety (II)

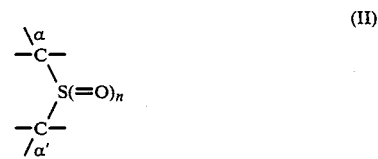

wherein in the sulfoxide n is 1 and in the sulfone n is 2, effecting the isotopic replacement by a known method of said at least one hydrogen atom, and reducing the resultant isotope-labelled sulfoxide or sulfone to the correspondingly labelled compound containing the structural moiety (I).

25 Claims, No Drawings

PROCESS FOR LABELLING SULFUR-CONTAINING COMPOUNDS

FIELD OF THE INVENTION

The present invention relates to a process for replacing hydrogen atoms in a thioether by deuterium or tritium.

BACKGROUND OF THE INVENTION

For many reasons connected with investigations into the mechanism of chemical and physiological reactions, and more particularly in connection with the manner of action of chemotherapeutic agents in the animal or human body, it is frequently desirable to label organic compounds with isotopes in place of the corresponding atoms originating in nature, that is in place of the atoms containing the natural distribution of isotopes.

Thus, deuterium and tritium, which are isotopes of hydrogen, have found wide application as tracers. The value of such a tracer generally arises from the fact that although its difference in mass (deuterium) or its radioactivity (tritium)—as compared with the regular hydrogen atom—permits its detection, its chemical behaviour is expected to resemble very closely that of the atoms which it has displaced. Notwithstanding that reactions involving the isotopes of hydrogen proceed at slightly but nevertheless measurably different rates, and therefore caution may be necessary in the precise interpretation of investigative results, it is still the case that the chemistry of all the isotopes of hydrogen is basically the same, qualitatively.

A problem which frequently arises in the case of an isotopically-labelled organic compound stems from the fact that the investigator generally desires to be able to trace a labelled atom, which is located in a specific position in the molecular structure. In order to place an isotope in a desired position, it may be necessary to undertake a complicated synthesis, which can be time-consuming and low-yielding, and consequently relatively expensive. Again, where the investigator is concerned with a particular stereoisomer, a difficult separation could be involved, additionally.

The principal object of the present invention is to provide a process by means of which hydrogen atoms in a particular position in a certain class of compounds, may be economically replaced by deuterium or tritium. A further object of the invention is to provide a process for preparing thus-labelled compounds within this class, which are enriched in, or which substantially consist of, a particular geometrical isomer or enantiomer, without requiring any separation of isomers other than that which has already been undertaken in respect of the unlabelled compound. Other objects of the invention will become apparent as the description proceeds.

SUMMARY OF THE INVENTION

The invention thus provides a process for the replacement by isotopes, of at least one of the hydrogen atoms selected from the group consisting of those attached to the α- or α'-carbon atom in a compound containing the structural moiety (I)

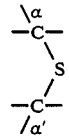

which comprises the steps of oxidizing the compound to the corresponding sulfoxide or sulfone which contains the corresponding structural moiety (II)

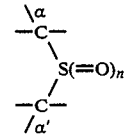

wherein in the sulfoxide n is 1 and in the sulfone n is 2, effecting the isotopic replacement by a known method of said at least one hydrogen atom, and reducing the resultant isotope-labelled sulfoxide or sulfone to the correspondingly labelled compound containing the structural moiety (I).

In a particular embodiment of this process, one of the carbon atoms α and α' may be substituted by a single nonpolar monovalent substituent group, whereby preferential isotopic replacement of at least one hydrogen atom attached to the other one of the carbon atoms α and α' is thereby effected.

DETAILED DESCRIPTION OF THE INVENTION

The starting material which contains the structural moiety (I) may be an aliphatic, alicyclic or aromatic compound. As examples of aliphatic and alicyclic compounds, there may be cited, for example, di-n-propyl sulfide and ethylthiocyclohexane, respectively. In aromatic compounds, the moiety (I) will form part of a side-chain, as e.g. in dibenzyl sulfide or methylthiomethylbenzene. Heterocyclic compounds are, however, the preferred starting materials. It will be appreciated that in this case the moiety (I) may form part of a side-chain, as for example in methylthiomethyltetrahydrofuran, or alternatively moiety (I) may constitute an integral part of a heterocyclic ring, as for example in the compounds tetrahydrothiophene, tetrahydrothiapyran, and their alkyl-substituted homologues.

Also within the scope of the present invention as starting materials, which contain isotope-replaceable hydrogen atoms attached to carbon atoms adjacent to a sulfur atom, are heterocyclic compounds in which a heterocyclic ring contains at least one further heteroatom in addition to the sulfur atom of said moiety (I). Examples of such starting materials are oxathiolane, oxathiane, dithiolane, dithiane, unfused hydrogenated thiazole and thiazine rings, and fused hydrogenated thiazole and thiazine rings. Penicillins and cephalosporins are well-known examples of azetidine-fused hydrogenated thiazole and thiazine rings, in which the fused-ring structures are generally referred to as penam, cephem or cepham ring systems.

Where in aliphatic, alicyclic, aromatic or heterocyclic compounds containing moiety (I), either one or other (but not both) of the α- and the α'-carbon atoms is fully substituted, then it is of course obvious that in absence of other factors, the isotope exchange reaction will take place at the α- or α'-carbon atom which is not fully substituted, i.e. to which there is attached at least one hydrogen atom. It will of course be necessary to block off competing sites for isotope exchange (if any such exist in the molecular structure of the starting material in question), but this is believed to be within the competence of persons skilled in the art.

Of particular interest are a family of compounds which contain a skeleton, part of which may be represented by moiety (IIIa). This formula shows a 1,3-oxathiolane structure, the ring positions of which have been indicated by numbers 1–5, in which R' and R'' are the same or different substituent groups, or one of them may be a hydrogen atom, and n is zero; the carbon valences at position 5 are taken up as described below. In this

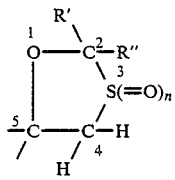

(IIIa: n = 0)

(IIIb: n = 1 or 2)

connection, it may be mentioned that many such compounds are described and claimed in European Patent Application 0205247, published Dec. 17, 1986, of which the present inventors were co-inventors, and the contents of which are incorporated herein by reference. When such compounds in which one of R' and R'' is a substituent and the other of which is a hydrogen atom are submitted to the process of the present invention, which requires the production of (IIIb) as an intermediate, it might have been expected that isotope-substitution would have occurred at position 2 rather than position 4, owing to the anticipated activation of the hydrogen atom in this position both by the sulfone or sulfoxide radical and by the adjacent oxygen atom (c.f. the activation of the hydrogen atoms attached to α-carbon in ethers, for example), whereas the hydrogen atoms in position 4 would be activated only by the sulfone or sulfoxide radical. However, the inventors made the surprising discovery that both hydrogen atoms in the 4-position in the moiety (IIIb) were susceptible to substitution by deuterium or tritium, in preference to the hydrogen atom in the 2-position. While neither the process of the invention in general, nor this particular embodiment of the process, are to be limited by any theory, nevertheless it would seem that steric factors play a part in preventing isotope replacement in position 2 of structure (IIIb).

As a consequence of the results described in the foregoing paragraph, it is believed that where in a starting material containing the moiety (I) generally, one of the carbon atoms α and α' is substituted by a single nonpolar ring-substituent (e.g. hydrocarbyl such as alkyl), then preferential isotopic replacement of at least one hydrogen atom attached to the other one of the carbon atoms α and α' will be effected, when carrying out the process of the invention. Moreover, when in the starting material there is a 1,3-oxathiolane ring in which one of the hydrogen atoms attached to carbon atoms in the 2- and 4-positions is substituted by a single nonpolar ring-substituent, then preferential isotopic replacement of at least one hydrogen atom attached to the other one of the 2- and 4-carbon atoms should occur. It will be further appreciated that whichever of the 2- or 4-carbon atoms carries the said ring-substituent will be asymmetric, so that in this instance the process of the invention may be carried out with a starting material which is enriched in respect of a particular stereoisomer. The 1,3-oxathiolane ring may or may not be further substituted, namely in the 5-position.

We have found that in carrying out the process of the invention on 1,3-oxathiolane derivatives, it is possible to isolate, in particular, intermediate sulfoxides (n=1) containing the moiety (IVb) and end products containing the moiety (IVa), where R' and R'' have the general meanings discussed previously and X is either D or $^3$H:

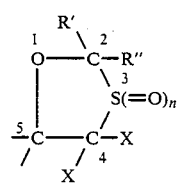

(IVa: n = 0)

(IVb: n = 1 or 2)

Compounds of therapeutic interest are known which contain a 1,3-oxathiolane ring, in which the 5-carbon atom is a spiro carbon atom. The other ring-system connected to this carbon atom may be for example a polyalkyleneimine or quinuclidine. Such spiro-polyalkyleneimine/oxathiolanes are described and claimed, for example, in European Patent Application 0189370, published Jan. 8, 1986 (Bolliger), the contents of which are incorporated herein by reference. Spiro quinuclidine/oxathiolanes are described and claimed, for example, in the above-mentioned European Patent Application 0205247. In the latter, the 3-position of the quinuclidine defines the same carbon atom as that at the 5-position of the oxathiolane ring.

A preferred starting material of the type just referred to, for use in the present process, is 2-methylspiro(1,3-oxathiolan-5,3')quinuclidine (V) and the obtained end-products in this instance will be 4-deuterated and 4-tritiated derivatives of (V), e.g. the 4-dideutero and 4-ditritio derivatives. Particularly preferred is a starting material (V) which has been enriched in a form selected from the (+)-, (+)- and (−)-cis-isomers and the (+)-, (+)- and (−)-trans-isomers, e.g. (V) which is at least about 95% enriched in said form. Compound (V) which has been enriched in the (+)-cis- or -trans isomers is described in the above-mentioned European Patent Application 0205247, as well as in Israel Patent Application No. 81652 (04627), the contents of which are incorporated herein by reference. The (+)- and (−)-cis- and -trans-isomers of (V) are described and claimed in our copending U.S. patent application Ser. No. 084,799 as filed Aug. 13, 1987, the contents of which are incorporated herein by reference.

At this point it should again be emphasized, that in contrast to the usual prior art methodology for placing a deuterium or tritium atom in a particular position of a molecular structure, which requires an unambiguous (and generally multistep) synthetic route, the present process affords a relatively simple manner of achieving the same object. The advantage is of course especially pronounced where particular stereoisomeric forms are concerned, insofar as previously separated stereoisomeric forms may be used directly as starting materials, and any separation of stereoisomers at the end of a tedious synthetic process is avoided. Confirmation that deuterium or tritium have in fact been placed in the desired positions can of course be checked by physical measurement, as is well-known.

As will be appreciated by those skilled in the art, the individual steps of the process of the invention, taken separately, and comprising the operations of oxidation, isotope replacement and reduction, are known per se. It is accordingly within the scope of the process of the invention to use any relevant known methods for the oxidation of thioethers to sulfoxides and sulfones, for the replacement of hydrogen atoms by deuterium or tritium atoms, and for the reduction of the labelled sulfoxides or sulfones back to the thioethers.

As examples only of reagents which may be used for these steps, there may be mentioned effecting the oxidation step by means of hydrogen peroxide, the isotopic replacement step by means of $D_2O$ or $^3H_2O$ under alkaline conditions, and the reduction step is by means of a complex hydride or a dithionite.

In the foregoing description, particular emphasis has been placed on the embodiment of the process which utilizes as starting materials, compounds containing 1,3-oxathiolane rings wherein the 2- or 4-carbon atom is monosubstituted. However, in a further embodiment of the process, either the 2- or 4-carbon atom in such structures may be disubstituted, and the other of the 2- and 4-carbon atoms may be unsubstituted, in which case the isotope substitution will of course normally be effected at that other (unsubstituted) carbon atom. In a particular aspect of this further embodiment, the 2-carbon atom is disubstituted, whereby preferential isotopic replacement of at least one hydrogen atom attached to the 4-carbon atom is thereby effected. The process may of course be effected on such a starting material which is enriched in respect of a particular stereoisomeric form thereof (e.g. a geometrical isomer, an enantiomer, a diastereoisomer or a racemate), and especially such a starting material which is at least about 95% enriched. Whether or not enriched material of this type is utilized, it will be evident that the 1,3-oxathiolane ring may contain additionally at least one substituent in the 5-position, e.g. the 5-carbon atom may be a spiro carbon atom in which the other ring system attached at this position may be e.g. a polyalkleneimine or quinuclidine, and especially a quinuclidine ring-system of which the 3-position defines the same carbon atom as that at the 5-position of the oxathiolane ring, as discussed previously. By this means, corresponding 4-dideutero and 4-ditritio derivatives may be obtained. Particular examples of compounds containing the structural moiety (IIIb) are claimed (inter alia) in our copending U.S. patent application Ser. No. (05330).

The present invention will now be illustrated by the following non-limitative Examples.

EXAMPLE 1

Preparation of sulfoxides from 2-methylspiro(1,3-oxathiolan-5,3')quinuclidine (V).

(a) (+)-cis-(V).HCl (18.9 g., 0.08 mol.) was dissolved in 200 ml. acetic acid and 25 ml. 30% hydrogen peroxide was added at room temperature. The mixture was stirred for 30 minutes, basified with 20% aqueous sodium hydroxide, and extracted with chloroform (3×200 ml.). The chloroform extracts were dried ($MgSO_4$) and evaporated to give 16.2 g. (94% yield) of a white powder which comprised a 1:1 mixture of (+)-cis-(V)-cis- and -trans-sulfoxides. The crude product (10 g.) was purified by chromatography on 250 g. silica, using 17:13:3:0.4 chloroform/petroleum ether/ethanol/28% aq. $NH_3$, to give 3.7 g. (+)-cis-(V)-trans-sulfoxide, 3 g. of a mixture of (+)-cis-(V)-cis- and -trans-sulfoxides and 2.2 g. (+)-cis-(V)-cis-sulfoxide.

(+)-cis-(V)-trans-sulfoxide $^1$H-NMR ($CDCl_3$-TMS) $\delta=1.7$ (d, 3H $CH_3$) (J=6.3 Hz); 1.3-2.1 (m, 5H); 2.56 (d, 1H) (J=14 Hz); 3.34 (d, 1H) (J=14 Hz); 2.6-3.2 (m, 6H); 4.7 (q, 1H) (J=6.3 Hz).

MS: M+ 215; base peak m/e 96.

High resolution molecular weight determination—calc. for $C_{10}H_{17}NSO_2$: 215.0978; found: 215.1055.

$^{13}$C-NMR ($CDCl_3$-TMS) $\delta=16.5$ ($CH_3$); 58.0 ($C_4$); 87.7 ($C_5$); 102.5 ($C_2$).

(+)-cis-(V)-cis-sulfoxide

1H-NMR ($CDCl_3$-TMS) $\delta=1.55$ (d, 3H $CH_3$) (J=6.3 Hz); 1.3-2 (m, 5H); 2.8 (d, 1H) (J=14 Hz); 3.6 (d, H) (J=14 Hz); 4.58 (q, 1H) (J=6.3 Hz).

MS; M+ 215; base peak m/e 96.

High resolution molecular weight determination—calc. for $C_{10}H_{17}NSO_2$: 215.0978; found: 215.0930.

$^{13}$C-NMR ($CDCl_3$-TMS) $\delta=12.64$ ($CH_3$); 82.3 ($C_4$); 85.6 ($C_5$); 91.7 ($C_2$).

(b) (+)-trans-(V).HCl was oxidized, and the resultant product was separated, as in part (a), above. The following were isolated.

(+)-trans-(V)-trans-sulfoxide $^1$H-NMR ($CDCl_3$-TMS) $\delta=1.66$ (d, 3H $CH_3$) (J=6 Hz); 4.72 (q, 1H) (J=6 Hz).

MS: M+ 215; base peak m/e 96.

High resolution molecular weight determination—calc. for $C_{10}H_{17}NSO_2$: 215.0978; found: 215.0985.

(+)-trans-(V)-cis-sulfoxide $^1$H-NMR ($CDCl_3$-TMS) $\delta=1.63$ (d, 3H $CH_3$) (J=6 Hz); 4.65 (q, 1H) (J=6 Hz).

MS: M+ 215; base peak m/e 96.

High resolution molecular weight determination—calc. for $C_{10}H_{17}NSO_2$: 215.0978; found: 215.1013.

EXAMPLE 2

Preparation of deuterated (+)-cis-(V)-trans-sulfoxide (+)-cis-(V)-trans-sulfoxide (0.9 g., 4.2 mmol.) was dissolved in 3.8 g. $D_2O$ and the exchange was performed under basic conditions with sodium hydroxide (0.2 g., 5 mmol.). The reaction mixture was left at 25° C. for 60 hours, extracted with chloroform (2×10 ml.), and the chloroform was dried and evaporated to yield 0.85 g. of pure deuterated sulfoxide.

$^1$H-NMR ($CDCl_3$-TMS) $\delta=1.7$ (d, 3H $CH_3$) (J=6.3 Hz); 4.69 (q, 1H) (J=6.3 Hz).

MS is enclosed M=217; base peak m/e 96.

$^{13}$C-NMR ($CDCl_3$-TMS) $\delta=16.5$ ($CH_3$); 67.6 ($C_5$); 102.5 ($C_2$).

EXAMPLE 3

Preparation of deuterated (+)-cis-(V)

(a) Deuterated (+)-cis-(V)-trans-sulfoxide (0.45 g. in 2 g. $D_2O$) was acidified using 4 ml. of 10% hydrochloric acid, and reduced at 50° C. for 1 hour with sodium dithionite (2 g. of 85%). The mixture was cooled, basified and extracted with chloroform (2×10 ml.). The chloroform extracts were dried and evaporated, and the residue was dissolved in 50 ml. hexane and precipitated with hydrogen chloride to give 0.2 g. of pure product in the form of the HCl salt.

$^1$H-NMR ($CDCl_3$-TMS) $\delta = 1.57$ (d, 3H $CH_3$) (J=6 Hz); 5.15 (q, 1H) (J=6 Hz).

MS is enclosed M+ 201; base peak m/e 96.

$^{13}$C-NMR ($CDCl_3$-TMS) $\delta = 22.4$ ($CH_3$); 80.4 ($C_2$); 83.9 ($C_5$).

(b) The same starting material (0.9 g.) was reduced with $LiAlH_4$. After work-up a 69% yield of pure title product (isolated as the HCl salt) was obtained.

MS studies based on the data obtained according to Examples 1-3 show addition of two mass units (exchange of two hydrogen atoms by deuterium). The type of fragmentation can be explained by exchange of hydrogen atoms on the five-membered ring. $^{13}$C NMR studies show disappearance of the large $C_4$ resonance and appearance of a multiplet instead, thus indicating that the hydrogen atoms near $C_4$ were substituted by deuterium. $^1$H NMR of the deuterated (V) emphasizes that (a) no isomerization takes place during reaction, and (b) no exchange of hydrogen takes place during the labelling step since the integration ratio between the $CH_3$ and H remains 3:1.

EXAMPLE 4

Preparation of tritiated (+)-cis-(V)-trans-sulfoxide (+)-cis-(V)-trans-sulfoxide (0.45 g., 2.1 mmol.) was dissolved in 2.2 ml. $^3H_2O$ (50 Ci/ml.). Sodium hydroxide (0.2 g.) was added and the mixture was left at room temperature for 70 hours. The title product as thus formed was used for Example 5 without isolation.

EXAMPLE 5

Preparation of tritiated (+)-cis-(V)

The solution obtained in Example 4 was acidified with 4 g. of 10% aqueous HCl, and 2 g. of 85% sodium dithionite was added. The clear solution was stirred at 50° C. for one hour, cooled and then basified with 3 g. 20% w/w aqueous sodium hydroxide. The mixture was extracted with chloroform (1×20 ml.), the extract was transferred into 200 ml. hexane, 0.7 g. 0.5M HCl in isopropanol was added to pH ~3 and the precipitate was filtered and dried to give 0.35 g. (1.5 mmol.) of the title product (71% yield) as the HCl salt. Specific activity: 543 mCi/mmole, total activity 823 mCi.

The product was checked by TLC using chloroform-petroleum ether-ethanol-ammonia 17:13:4:0.4 to give one spot $R_f = 0.4$ which was detected as a brown spot on exposure to $I_2$ vapor. Radiochemical purity was determined using the same plate.

The HCl salt was dissolved in water containing 5% ethanol 10 mCi/ml. and kept at 4° C.

Tritiated (+)-cis-(V) and its corresponding isolated enantiomers can be used as radioactive ligands in receptor binding studies, since they would be expected to bind to $M_1$ muscarinic receptors. Such a probe can be utilized both in displacement studies and in autoradiography of $M_1$ receptors in animal and human brain samples taken at autopsy or biopsy. In addition, they can be used in pharmacokinetic studies in experimental animals.

Deuterated (+)-cis-(V) and its corresponding isolated enantiomers can be used as an internal standard in pharmacokinetic studies in experimental animals and can also be used in the disease states described in European Patent Application No. 0205247.

While the invention has been particularly described with especial reference to the Examples, it will be appreciated by those skilled in the art that many variations in and modifications of the process of the invention may be made. The invention is accordingly not to be construed as limited by the matter particularly described, rather it will be defined as set out in accordance with the claims which follow.

We claim:

1. A process for obtaining the replacement by isotopes of at least one of the hydrogen atoms selected from the group consisting of those attached to the α- or α'-carbon atom in a heterocyclic compound containing the structural moiety (I)

as an integral part of a heterocyclic ring selected from the group consisting of 1,3-oxathiolane, 1,3-oxathiane, 1,3-dithiolane and 1,3-dithiane, in preference to isotopic replacement of hydrogen atoms attached to carbon atoms in said compound other than said α- and α'-carbon atoms, which process comprises the steps of oxidizing the compound to the corresponding sulfoxide or sulfone which contains the corresponding structural moiety (II)

wherein in the sulfoxide n is 1 and in the sulfone n is 2, effecting the isotopic replacement by a known method of said at least one hydrogen atom, and reducing the resultant isotope-labelled sulfoxide or sulfone to the corresponding isotopically labelled compound containing the structural moiety (I), in which labelled compound isotopes of hydrogen are attached to at least one carbon atom selected from the group consisting of said α- and α'-carbon atoms.

2. A process according to claim 1, wherein one of the carbon atoms α and α' is substituted by a single nonpolar monovalent substituent group, whereby preferential isotopic replacement of at least one hydrogen atom attached to the other one of the carbon atoms α and α' is thereby effected.

3. A process according to claim 1, wherein one of the carbon atoms α and α' is fully substituted, whereby preferential isotopic replacement of at least one hydrogen atom attached to the other one of the carbon atoms α and α' is thereby effected.

4. A process according to claim 1, wherein said heterocyclic ring is a 1,3-oxathiolane ring, in which at least one of the hydrogen atoms attached to one only of the carbon atoms selected from the group consisting of those in the 2- and 4-positions is substituted by a single nonpolar ring-substituent, whereby preferential isotopic replacement of at least one hydrogen atom attached to the other one of the 2- and 4-carbon atoms is effected.

5. A process according to claim 4, wherein the starting material contains the structural moiety (IIIa), in which R' and R" are the same or different substituent groups, or one of them

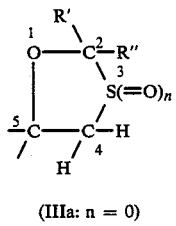

(IIIa: n = 0)

(IIIb: n = 1 or 2)

may be a hydrogen atom, and the product of the initial oxidation step contains the structural moiety (IIIb).

6. A process according to claim 5, wherein the product of the step of labelling the intermediate containing the structural moiety of formula (IIIb) contains a structural moiety of formula

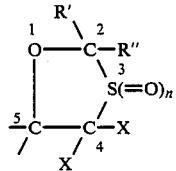

(IVa: n = 0, X = D or tritium)

(IVb: n = 1 or 2, X = D or tritium)

(IVb), and the end product contains a structural moiety of formula (IVa).

7. A process according to claim 6, wherein one of R' and R" is a substituent and the other of them is a hydrogen atom.

8. A process according to claim 7, wherein the 5-position is substituted.

9. A process according to claim 8, wherein the 5-carbon atom is a spiro carbon atom.

10. A process according to claim 9, wherein the ring-system connected by a spiro-attachment at the 5-position is a ring-system selected from the group consisting of polyalkyleneimines and quinuclidine.

11. A process according to claim 10, wherein the said ring-system is quinuclidine, and the 3-position thereof defines the same carbon atom as that at the 5-position of the oxathiolane ring.

12. A process according to claim 6, wherein each of R' and R" are the same or different substituents.

13. A process according to claim 12, wherein the 5-position is substituted.

14. A process according to claim 13, wherein the 5-carbon atom is a spiro carbon atom.

15. A process according to claim 14, wherein the ring-system connected by a spiro-attachment at the 5-position is a ring-system selected from the group consisting of polyalkyleneimines and quinuclidine.

16. A process according to claim 15, wherein the said ring-system is quinuclidine, and the 3-position thereof defines the same carbon atom as that at the 5-position of the oxathiolane ring.

17. A process according to claim 7, which is effected on a starting material which is enriched in respect of a particular stereoisomer thereof.

18. A process according to claim 12, which is effected on a starting material which is enriched in respect of a particular stereoisomer thereof.

19. A process according to claim 1, wherein the starting compound is 2-methylspiro(1,3-oxathiolan-5,3')quinuclidine (V).

20. A process according to claim 19, wherein the starting material is (V) which has been enriched in a form selected from the group consisting of the (+)-, (+)- and (−)-cis-isomers and the (+)-, (+)- and (−)-trans-isomers.

21. A process according to claim 20, wherein the starting material is at least about 95% enriched in said form.

22. A process according to claim 1, wherein said oxidizing step is effected by means of hydrogen peroxide.

23. A process according to claim 1, wherein said isotopic replacement step is effected by means of $D_2O$ or $^3H_2O$ under alkaline conditions.

24. A process according to claim 1, wherein said reducing step is effected by means of a complex hydride or a dithionite.

25. A process according to claim 1, wherein said oxidizing step is effected by means of hydrogen peroxide, said isotopic replacement step is effected by means of $D_2O$ or $^3H_2O$ under alkaline conditions, and said reducing step is effected by means of a complex hydride or a dithionite.

* * * * *